United States Patent
Rogers (10) Patent No.: US 7,832,395 B2
(45) Date of Patent: Nov. 16, 2010

(54) PORTABLE OXYGEN DELIVERY APPARATUS

(75) Inventor: Bruce Rogers, Hailey, ID (US)

(73) Assignee: Oxygen Plus, Inc., Mahtomedi, MN (US)

( * ) Notice: Subject to any disclaimer, the term of this patent is extended or adjusted under 35 U.S.C. 154(b) by 846 days.

(21) Appl. No.: 11/715,828

(22) Filed: Mar. 8, 2007

(65) Prior Publication Data

US 2007/0215153 A1    Sep. 20, 2007

Related U.S. Application Data (60) Provisional application No. 60/780,612, filed on Mar. 9, 2006.

(51) Int. Cl.
*A62B 7/00*    (2006.01)

(52) U.S. Cl. .............. 128/200.24; 128/205.25; 128/205.24; 128/200.14; 128/200.23

(58) Field of Classification Search ............ 128/203.23, 128/200.23, 200.12, 200.24, 202.26, 203.24, 128/204.18, 205.21, 205.22, 205.26, 206.26; 422/120, 121, 123, 124, 125, 126; 206/6
See application file for complete search history.

(56) References Cited

U.S. PATENT DOCUMENTS

| | | | |
|---|---|---|---|
| 3,045,671 A | | 7/1962 | Updegraff |
| 3,736,928 A | * | 6/1973 | Andersson et al. ..... 128/206.19 |
| 3,776,227 A | | 12/1973 | Pitesky et al. |
| 4,047,645 A | * | 9/1977 | Caliendo ............... 222/386.5 |
| 4,062,357 A | * | 12/1977 | Laerdal ................ 128/206.26 |
| 4,465,067 A | | 8/1984 | Koch et al. |
| 4,559,941 A | | 12/1985 | Timmons et al. |
| 4,583,246 A | * | 4/1986 | Griswold .................. 2/2.14 |
| 4,671,270 A | * | 6/1987 | Kato ..................... 128/202.26 |
| 4,685,456 A | | 8/1987 | Smart |
| 4,996,983 A | | 3/1991 | AmRhein |
| 5,193,534 A | | 3/1993 | Peppler |
| 5,318,019 A | * | 6/1994 | Celaya .................. 128/204.26 |
| 5,370,647 A | * | 12/1994 | Graber et al. ............... 606/127 |
| 5,465,712 A | * | 11/1995 | Malis et al. ............ 128/205.25 |
| 5,505,194 A | * | 4/1996 | Adjei et al. ............ 128/200.23 |
| 5,571,246 A | | 11/1996 | Alldredge |
| 5,582,164 A | | 12/1996 | Sanders |
| 5,836,953 A | * | 11/1998 | Yoon ......................... 606/114 |
| 5,842,470 A | * | 12/1998 | Ruben .................. 128/206.19 |
| 6,379,312 B2 | | 4/2002 | O'Toole |
| 6,412,488 B1 | * | 7/2002 | Barnett et al. .......... 128/207.13 |
| 6,494,201 B1 | * | 12/2002 | Welik ..................... 128/200.23 |
| 6,494,202 B2 | * | 12/2002 | Farmer ................. 128/200.23 |
| 6,510,818 B2 | * | 1/2003 | Barney et al. ............... 119/831 |
| 6,510,850 B1 | | 1/2003 | Izuchukwu et al. |

(Continued)

*Primary Examiner*—Justine R Yu
*Assistant Examiner*—LaToya Louis
(74) *Attorney, Agent, or Firm*—Patterson Thuente Christensen Pedersen, P.A.

(57) ABSTRACT

A portable breathable gas delivery device including a pressure vessel for storing the breathable gas under pressure and a valve coupled to the pressure vessel through which the breathable gas can be selectively released. The pressure vessel is enclosed in a housing having a first portion that at least partially encloses the pressure vessel and a second portion that partially encloses a chamber coupled to the pressure vessel via the valve into which the breathable gas can be released for breathing by a user. The second portion together with a user's facial structure forms a substantially closed enclosure. The chamber has an opening shaped and formed to interface with the user's facial structure.

9 Claims, 9 Drawing Sheets

U.S. PATENT DOCUMENTS

| | | |
|---|---|---|
| 6,526,968 B1 | 3/2003 | Izuchukwu et al. |
| 6,845,772 B2 * | 1/2005 | Braithwaite et al. .... 128/203.15 |
| 7,204,246 B1 * | 4/2007 | Berinato ................. 128/200.14 |
| 7,341,056 B1 * | 3/2008 | Tucker .................. 128/200.14 |
| 2002/0121276 A1 * | 9/2002 | Genova et al. ......... 128/200.23 |
| 2003/0010336 A1 * | 1/2003 | Vito ...................... 128/200.22 |
| 2003/0121517 A1 * | 7/2003 | McFarland, Jr. ....... 128/200.14 |
| 2004/0255946 A1 * | 12/2004 | Gerson et al. .......... 128/205.27 |
| 2005/0005930 A1 * | 1/2005 | Rubel .................... 128/200.23 |
| 2005/0051172 A1 * | 3/2005 | Lee ....................... 128/206.19 |
| 2005/0194400 A1 | 9/2005 | Berube et al. |
| 2006/0272575 A1 * | 12/2006 | Monterrosa ................. 118/301 |

* cited by examiner

PORTABLE OXYGEN DELIVERY APPARATUS

CLAIM TO PRIORITY

This application claims priority to U.S. Provisional Application 60/780,612 entitled "Portable Oxygen Delivery Apparatus" filed Mar. 9, 2006 which is incorporated herein by reference.

FIELD OF THE INVENTION

The invention relates generally to an apparatus of supplying breathable gas such as oxygen or air to a person. More particularly, the present invention relates to an oxygen or air delivery apparatus that is portable.

BACKGROUND OF THE INVENTION

Clean air is an important part of maintaining health. Environments that contain air-borne pollutants and infectious agents have been the subject of much publicity and awareness in the recent past. Second-hand cigarette smoke, carbon monoxide, prominent publicity regarding Severe Acute Respiratory Syndrome (SARS), dust, pollen and automotive exhaust has raised public awareness of these issues. The listed pollutants, among others, can cause respiratory discomfort, disease, damage, or inefficiency.

Some of these effects can be temporary, as when exposed to an irritant or allergen where the effect disappears after the allergen is removed. Some of these effects can be permanent, as when second-hand cigarette smoke or radon causes lung cancer. It is beneficial to an otherwise healthy person to maintain a supply of high quality breathable air by either filtering the ambient air before inhalation, or by providing an alternate source for the breathable air that excludes a large fraction of ambient air.

It is well known that people who suffer from respiratory disease, such as emphysema, may pull a cart that bears an oxygen tank that supplies oxygen to an area around the nose or mouth in order to provide an enhanced oxygen supply to the damaged lungs. Another example is the use of oxygen masks in hospitals to provide oxygen support to persons needing it. These systems provide higher quality air in a manner that is not easily portable for an individual. The oxygen supply in these circumstances may be heavy, bulky and unsightly. An individual is therefore not likely to carry such a device unless forced to by medical necessity.

For the purposes of this application, higher quality air refers to air with either more desirable characteristics, fewer undesirable characteristics, or both. Percent of oxygen content, presence of particulates or pollen, aromatic compounds, gaseous and particulate carbon compounds including hydrocarbons, nitrogen containing compounds, carbon monoxide, ozone, viral infectious agents, bacterial infectious agents, sulfur containing compounds, dust, soot, smoke, smog, and many other compounds can, among many other factors, be used when determining air quality.

As air quality in many cities declines, and as the perception that the number and quantity of harmful components in the air is increasing, there is a growing group of people who wish to breathe higher quality air but who are unwilling to transport a large tank of higher quality air around in a cart.

In addition, breathing enhanced quality air or increased oxygen content air may have health benefits for athletes and active people. It is well known that atmospheric pressure and thus the partial pressure of oxygen available for breathing is reduced at higher altitudes. Whether hiking in the mountains or sitting in a commercial airliner reduced oxygen availability may make people feel fatigued, irritable or just out of sorts.

The health and wellness industry has begun to place an emphasis on making people who may already be in excellent health feel better. Spas and other facilities that pamper and comfort their clients are more and more common.

Further, some people have developed a desire to stop periodically in commercial locations called oxygen bars. Oxygen bars provide customers with, among other services, the opportunity to temporarily inhale higher quality air. However, such an establishment is not always nearby when a person has a desire to inhale higher quality air.

SUMMARY OF THE INVENTION

The present invention addresses many of the above discussed problems. A personal oxygen delivery apparatus generally includes a storage vessel and a delivery system. The storage vessel may be filled with oxygen, air or another breathable gas mixture and discharges the breathable gas or gas mixture via a valve assembly. Oxygen, air or other breathable gases are discharged and inhaled through the delivery system. The personal oxygen delivery apparatus is small and light weight so that it can easily be stored and transported.

A portable breathable gas delivery apparatus in accordance with an embodiment of the present invention generally includes a pressure vessel for storing the breathable gas under pressure and a valve coupled to the pressure vessel. The housing generally includes a first portion that at least partially encloses the pressure vessel and a second portion that partially encloses a chamber into which the valve can release the breathable gas. The partially enclosed chamber is shaped to cooperate with a user's facial structure to form a substantially enclosed area. The valve can be used selectively to release the breathable gas into a portion of a housing. Thus when the breathable gas is release into the chamber, the user can inhale and exhale, breathing the breathable gas from the chamber.

In one aspect of the invention, the storage vessel is telescopically receivable into the second portion of the housing for transport. The storage vessel can also be withdrawn from the second portion of the housing, thus making the second portion of the housing larger.

In some embodiments of the invention, the opening of the chamber is formed by a beveled edge of the substantially cylindrical second portion and is thus substantially oval in shape. The oval shape is convex adapted for interfacing with the user's facial structure.

In another aspect of the invention, the second portion of the housing is structured so that it can be shifted from a folded configuration to unfolded configuration. The unfolded configuration is appropriately shaped to interface with the user's face to allow breathing of the gas from the pressure cylinder. In one embodiment of the invention, the foldable second portion includes a plurality of generally ridged panels that are joined together by a plurality of flexible panels which then allows the chamber to expand or fold to accommodate the user's facial structure.

Another embodiment of the invention further includes a removable end cap which can be joined at the second portion when the second portion is in the folded state to close off the end of the second portion to exclude dirt and debris that may otherwise enter the second portion when the breathable gas delivery apparatus is in storage or transport.

In another aspect of the invention, the second portion includes a plurality of wing members that can be unfolded in order to accommodate a user's facial structure.

In yet another aspect of the invention, the second portion of the housing includes a storage lid, which is hingely attached to the housing. The storage lid is then shiftable between a first position and a second position, in the second position the storage lid in cooperation with the rest of the housing creates an oval opening into which the user's facial structure may be interfaced.

In another aspect of the invention, the portable breathable gas delivery apparatus includes a coupling structure such as a ring or clip. The ring or clip may be adapted to attach to a further structure for storage or transport. For example, the ring or clip may be used to attach the portable breathable gas delivery apparatus to a backpack, belt pack or some other structure.

In another aspect of the invention, the invention includes a method of providing breathable gas for delivery to an individual including storing the breathable gas under pressure releasing the breathable gas through a valve into an at least partially enclosed chamber so that the user may engage the partially enclosed chamber to their facial structure for breathing.

A person may desire to use a portable oxygen delivery apparatus even when the person is generally in good health. For example, it may be desirable to use the oxygen delivery apparatus in areas with decreased air quality such as may be caused by smog. It may also be desired to use the oxygen delivery apparatus to assist in recovery from performing physical activities. Another situation where an oxygen delivery apparatus may be used is in a fire to assist in retaining consciousness while evacuating from the fire.

DETAILED DESCRIPTION

An embodiment of the invention relates to a portable oxygen delivery apparatus, as illustrated at 10 in FIGS. 1-7. The portable oxygen delivery apparatus 10 has a compact design that enables the portable oxygen delivery apparatus 10 to be readily transported or stored until a desired use time.

Figure 1:
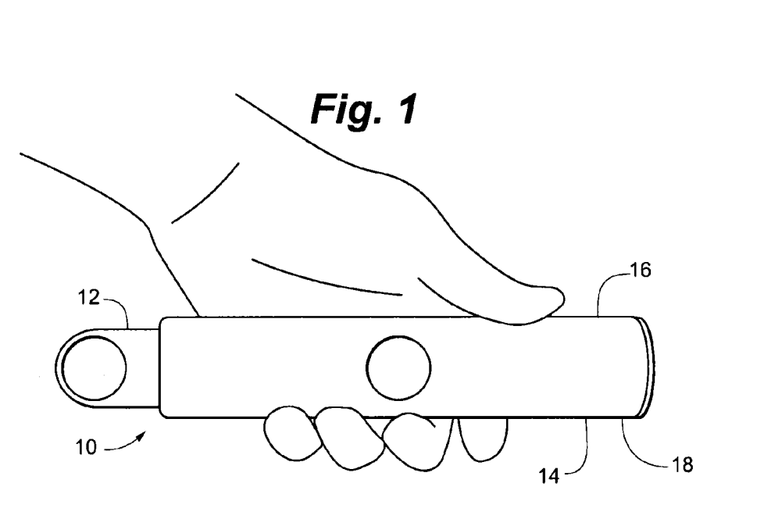
FIG. 1 is a side view of a portable oxygen delivery apparatus in the retracted configuration according to an embodiment of the invention.
Figure 2:
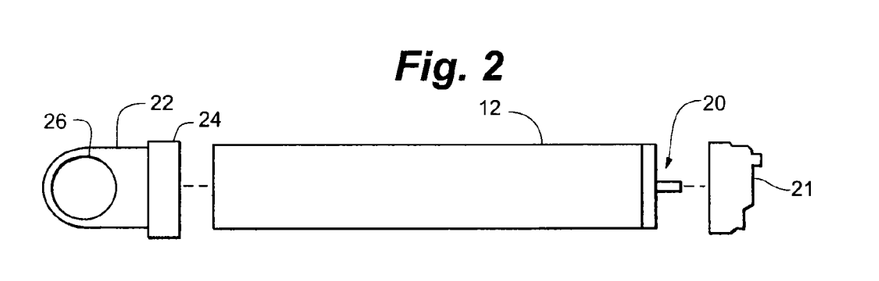
FIG. 2 is an exploded side view of a storage vessel of a portable oxygen delivery apparatus according to an embodiment of the present invention.
Figure 3:
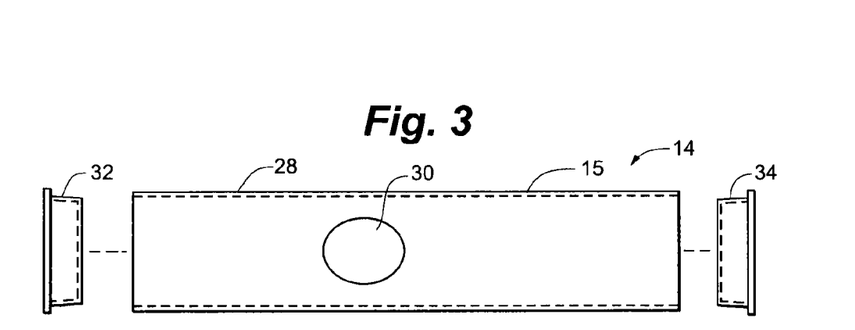
FIG. 3 is an exploded side view of a delivery system of a portable oxygen delivery apparatus according to an embodiment of the present invention.

In one aspect of the invention, portable oxygen delivery apparatus 10 generally includes storage vessel 12 and delivery system 14. Storage vessel 12 may be mounted within delivery system 14. Storage vessel 12 is fabricated from a material that is capable of withstanding and containing relatively high internal pressure to facilitate compressing the oxygen, air or other breathable gas stored therein. Compressing the breathable gas enhances the storage capacity of storage vessel 12 and thus the length of time during which it can provide a breathable air supply. Delivery System 14 includes housing 16 including chamber portion 18. Housing 16 encloses storage vessel 12 at least partially and further includes chamber portion 18.

Chamber portion 18 of housing 16 is an operable fluid communication with storage vessel 12, via valve assembly 20. Valve assembly 20 may be any appropriate valve assembly known to those of skill in the art for releasing gas from a storage vessel 12 and for facilitating filling of storage vessel 12.

Chamber portion 18 may vary in size, shape and structure. Chamber portion 18 partially encloses a chamber and has a margin adapted to interface with the mouth and nose area of a user to facilitate breathing gas released from storage vessel 12.

Storage vessel 12 is operably coupled to valve assembly 20 that is used for filling storage vessel 12 with oxygen and air as well as discharging the oxygen and air using delivery system 14. For many applications, valve assembly 20 is pressure activated. Valve assembly 20 may be activated by actuator 21.

In an embodiment of the invention, storage vessel 12 also may include handle 22 used to slide the storage vessel 12 into and out of delivery system 14. Handle 22 may further include connector portion 24 for connecting it to storage vessel 12 and ring 26. Although depicted as being circular, ring 26 can be given any number of shapes. Handle 22 may be a separate piece affixed to storage vessel 12, as shown in FIG. 2, or may be integrally formed with storage vessel 12.

The storage vessel 12 may also include a pressure indicator (not shown) that assists a user to evaluate the remaining supply of breathable gas in and thus the useful life of storage vessel 12. Examples of suitable pressure indicators include analog pressure gauges, digital pressure gauges and visual pressure indicators that may change between phrases such as OK and REPLACE.

Figure 4:
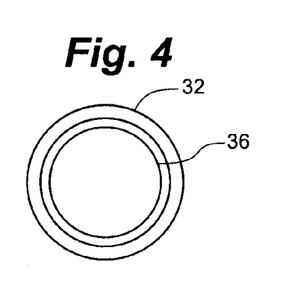
FIG. 4 is an end view of a first end cap of a delivery system according to an embodiment of the present invention.
Figure 5:
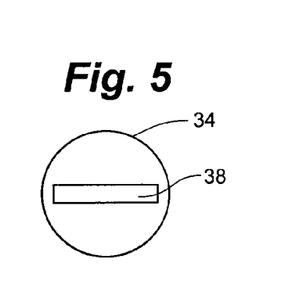
FIG. 5 is an end view of a second end cap of a delivery system according to an embodiment of the present invention.

In one aspect of the invention, delivery system 14 generally includes receiver 28 in which storage vessel 12 is slidably received. Receiver 28 further defines aperture 30 through one surface of the receiver 28. Although depicted as being a single, circular opening, aperture 30 can comprise a plurality of apertures and can be of any shape. Delivery system 14 also includes first end cap 32 and a second end cap 34. As can be seen in FIG. 4, first end cap 32 defines aperture 36. Aperture 36 is sized to receive storage vessel 12. Second end cap 34, depicted in greater detail in FIG. 5, includes breathing aperture 38.

Figure 8:
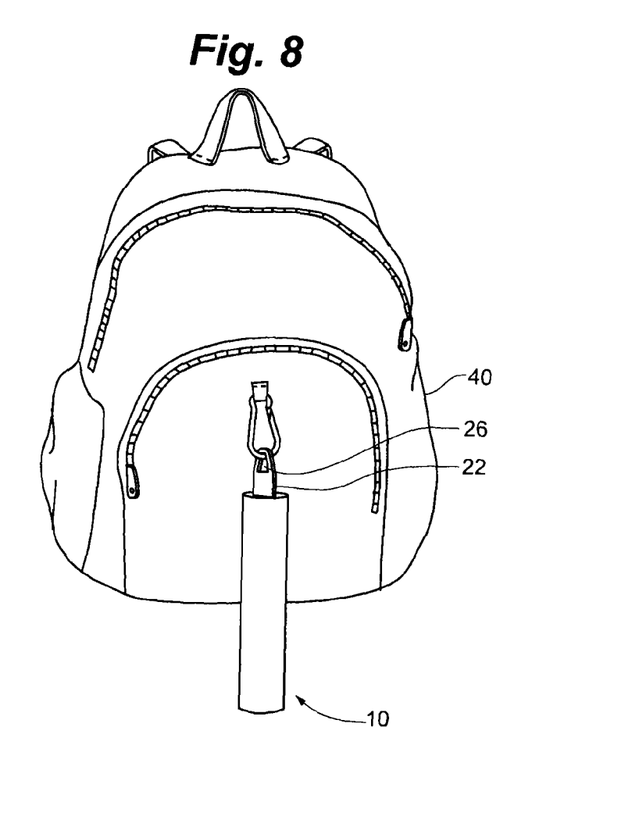
FIG. 8 is a front view of a portable oxygen delivery apparatus attached to an external object according to an embodiment of the present invention.

As can be seen in FIG. 8, portable oxygen delivery apparatus 10 may be configured to be attached to a backpack 40, suitcase, belt loop, or the like. Ring 26 can be provided with a hinged clip such that handle 22 functions like a carabineer or other similar clipping device. One of skill in the art will recognize numerous other ways in which handle may be configured to be attached to an object.

Figure 9:
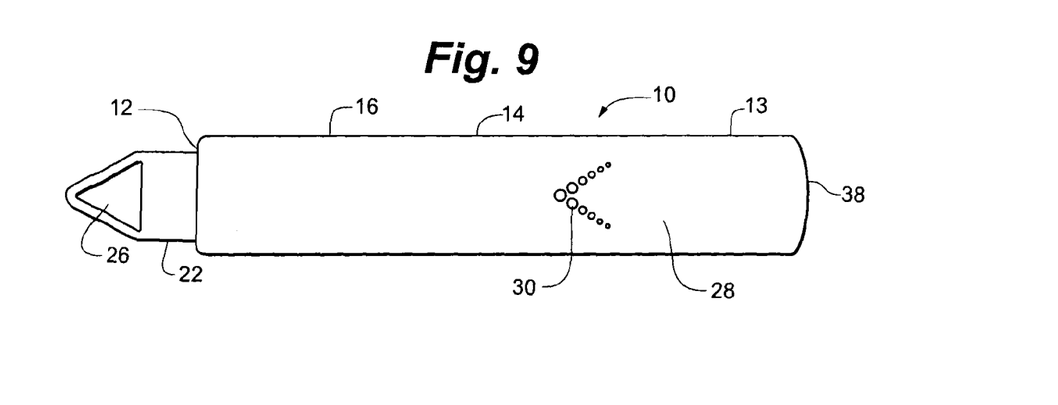
FIG. 9 is a side view of a portable oxygen delivery apparatus in a retracted configuration according to an embodiment of the present invention.

Referring now to FIG. 9, portable oxygen delivery apparatus 10 according to another embodiment of the present invention is depicted. As in other embodiments, portable oxygen delivery apparatus 10 includes storage vessel 12 and delivery system 14. However, handle 22 includes ring 26 that is triangular in shape, rather than circular. In addition, receiver 28 includes a plurality of small apertures 42, in addition to or instead of a single large aperture 38.

Figure 10:
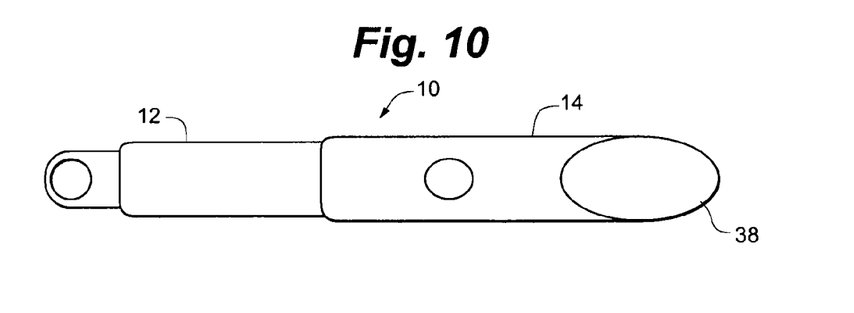
FIG. 10 is a side view of a portable oxygen delivery apparatus in an extended configuration according to an embodiment of the present invention.

Referring to FIG. 10, portable oxygen delivery apparatus 10 according to another embodiment of the present invention is depicted. Portable oxygen delivery apparatus 10 is substantially similar to embodiments of portable oxygen delivery apparatuses 10 described above, and generally includes storage vessel 12 and delivery system 14. In this embodiment, housing 16 an oval shaped breathing aperture at the end of chamber portion 18. One of skill in the art will recognize that the breathing aperture may take on a variety of shapes.

Figure 11:
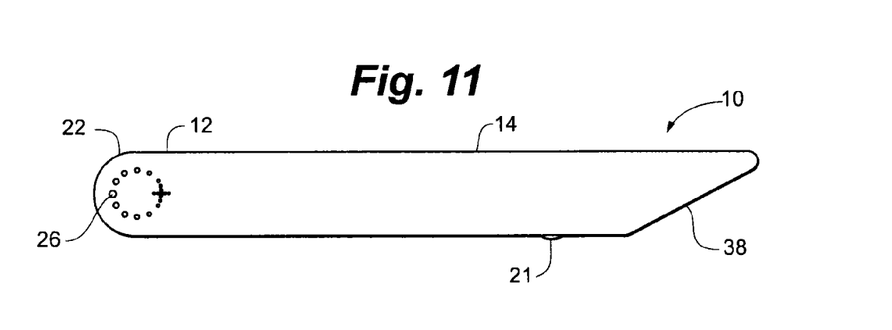
FIG. 11 is a side view of a portable oxygen delivery apparatus according to an embodiment of the present invention.
Figure 12:
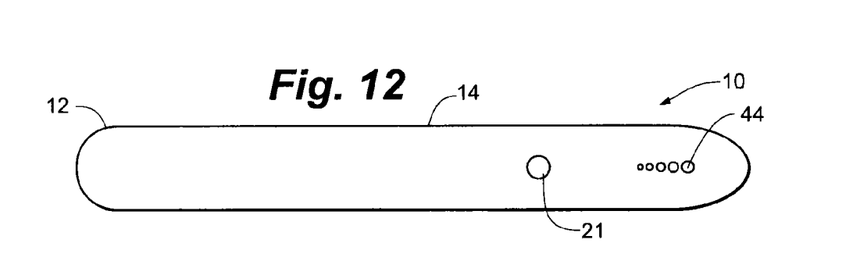
FIG. 12 is a top view of a portable oxygen delivery apparatus according to an embodiment of the present invention.

FIGS. 11 and 12 depict portable oxygen delivery apparatus 10 according to another embodiment of the present invention. In this embodiment, handle 22 of storage vessel 12 does not include a ring, but rather has a decorative design or indicia, such as a logo, printed thereon. Additionally, chamber portion of housing 18 has an oval shaped end with a plurality of circular apertures 44. One of skill in the art will recognize that the size, shape, and arrangement of the apertures may be varied.

Figure 13:
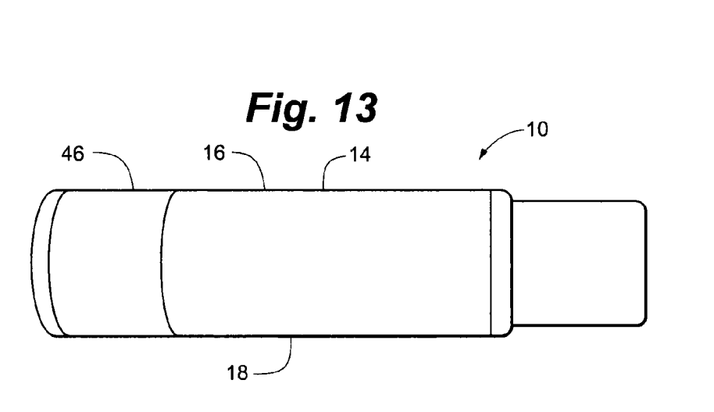
FIG. 13 is a side view of a portable oxygen delivery apparatus according to an embodiment of the present invention.
Figure 14:
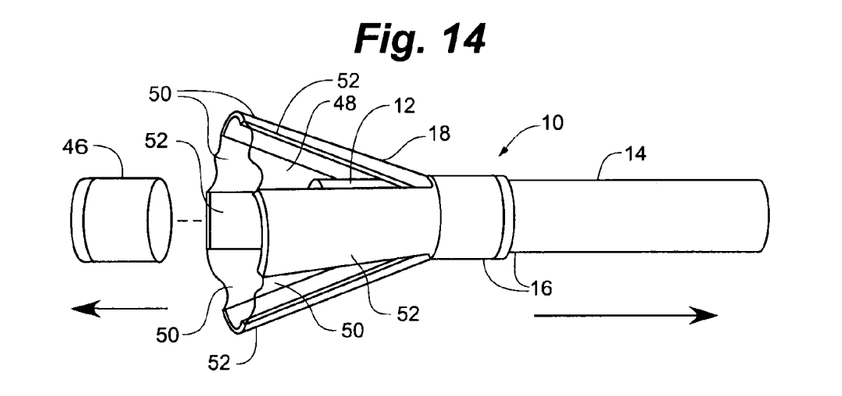
FIG. 14 is a perspective view of a portable oxygen delivery apparatus according to an embodiment of the present invention.
Figure 15:
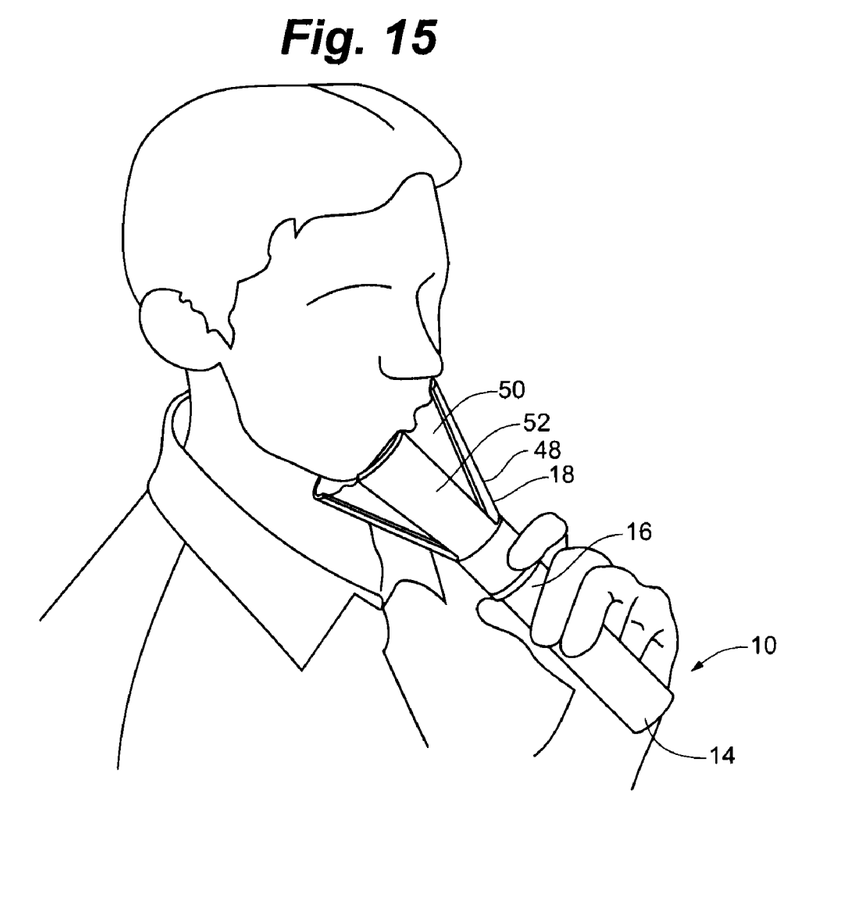
FIG. 15 is a perspective view of oxygen being dispensed from a portable oxygen delivery apparatus according to an embodiment of the present invention.

FIGS. 13-15 depict another portable oxygen delivery apparatus 10 according to a further embodiment of the present invention. Oxygen delivery apparatus 10 includes storage vessel 12, delivery system 14, and cap 46. Storage vessel 12 is contained substantially within delivery system 14 housing 16, and is removed only to insert a new storage vessel 12 when a previous one needs to be replaced. Delivery system 14 further includes a built-in mask 48 that is structured of a plurality of webs 50 connected to one another by connecting members 52. Connecting members 50 give webs 50 more strength and stability. Although depicted as having four webs 50 and four connecting members 52, portable oxygen delivery system can have greater or fewer webs and connecting members.

The embodiment depicted in FIGS. 13-15 is used by first removing cap 46. This allows connecting members 52 to be opened up which spreads webs 50. The user puts webs 50 around the mouth and/or nose when the storage vessel 12 is actuated creating a seal that prevents ambient air from mixing with the stored air. After use, webs 50 are folded back together and cap 46 is replaced.

Figure 16:
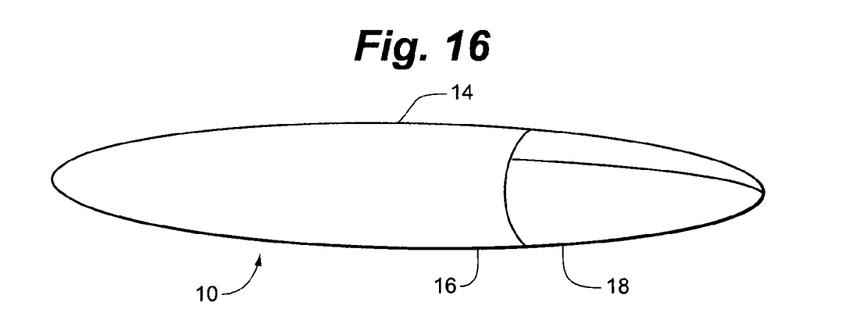
FIG. 16 is side view of a portable oxygen delivery apparatus in a storage configuration according to an embodiment of the present invention.
Figure 17:
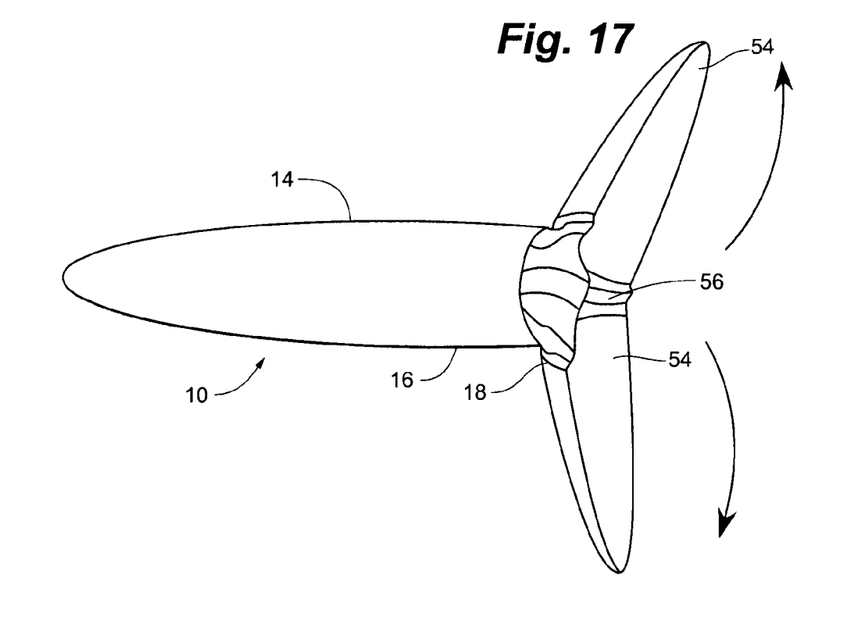
FIG. 17 is a side view of a portable oxygen delivery apparatus according to an embodiment of the present invention.

Referring to FIGS. 16 and 17, a portable oxygen delivery apparatus 10 according to another embodiment of the present invention is depicted. Here, portable oxygen delivery apparatus 10 is a one-piece design in which storage vessel 12 is contained within housing 14. Chamber portion 18 includes a pair of wings 54 that fold open to form a breathing opening 56. Although depicted as having two wings 54, portable oxygen delivery system 10 may have a greater or smaller number of wings 54. Wings 54 can be pressed against the face of the user to cover the nose and/or mouth to reduce the amount of ambient air inhaled by the user.

Figure 18:
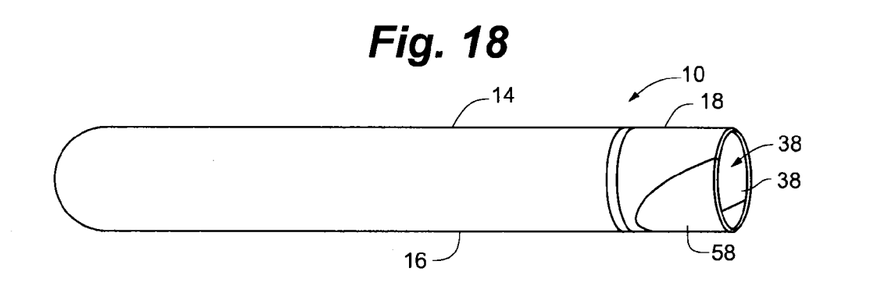
FIG. 18 is side view of a portable oxygen delivery apparatus in a storage configuration according to an embodiment of the present invention.
Figure 19:
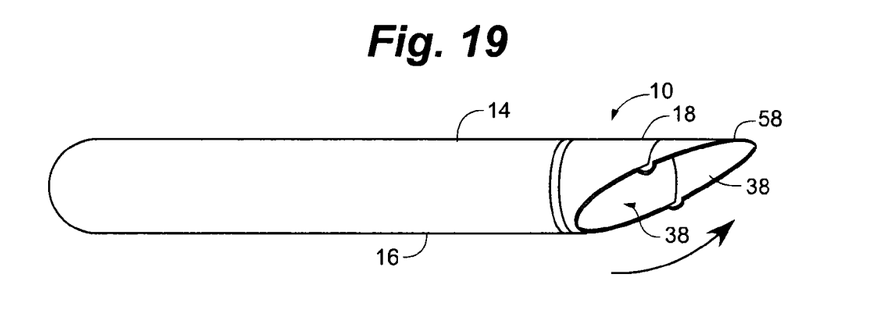
FIG. 19 is a side view of a portable oxygen delivery apparatus according to an embodiment of the present invention.

Another portable oxygen delivery apparatus 10 according to an embodiment of the present invention is depicted in FIGS. 18 and 19. Here, portable oxygen delivery apparatus 10 is a one-piece design. Portable oxygen delivery system 10 includes chamber portion 16 including hinged lid 58. Hinged lid 58. mat take the form of a section of a cylinder that have been cut on a diagonal. In storage, lid 58 is down and breathing aperture 38 is circular. When actuated, the lid 58 may be flipped up thereby make breathing aperture 38 oval-shaped. The user therefore has the option of breathing through a circular or an oval shaped breathing aperture 38.

Figure 6:
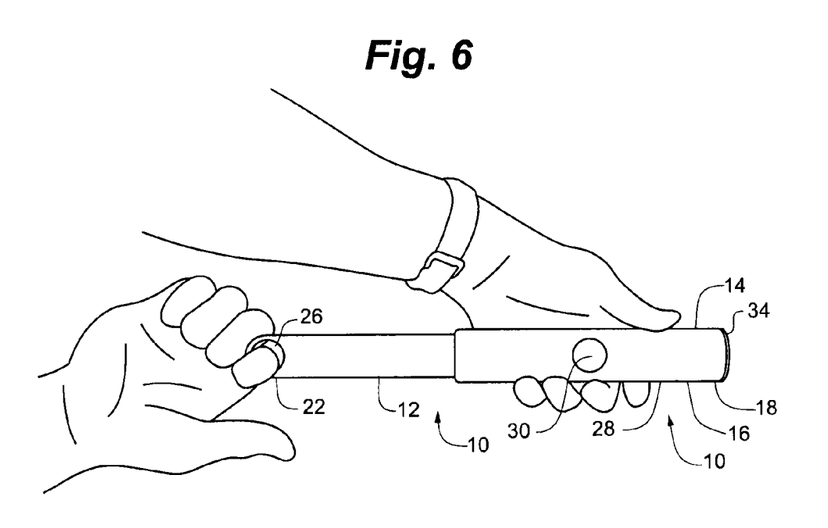
FIG. 6 is a side view of a portable oxygen delivery apparatus in the extended configuration according to an embodiment of the present invention.
Figure 7:
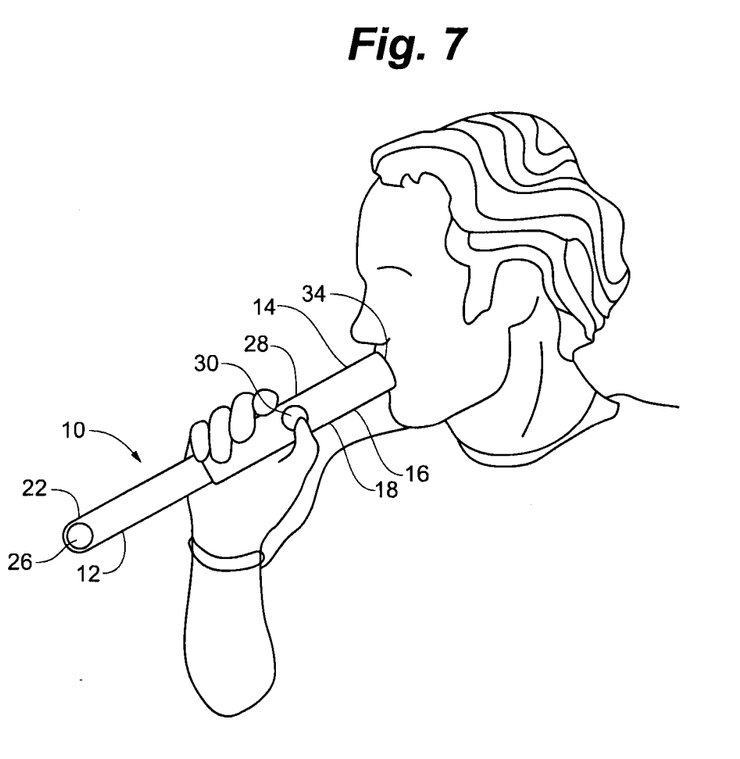
FIG. 7 is a perspective view of a portable oxygen delivery apparatus in position for oxygen to be dispensed according to an embodiment of the present invention.

Operation of some embodiments of the invention, portable oxygen delivery apparatus 10 can be more clearly understood with reference to FIGS. 1, 6, and 7. Portable oxygen delivery apparatus 10 is stored and transported in a retracted configuration as shown in FIG. 1. In the retracted configuration, storage vessel 12 rests substantially within delivery system 14. To use portable oxygen delivery apparatus 10, storage vessel 12 is withdrawn from delivery system 14 for example by placing a finger in ring 26 and pulling on handle 22.

Storage vessel 12 slides out of delivery system 14 until it encounters an internal stop (not pictured), leaving it approximately in the position shown in FIGS. 6 and 7. The internal stop (not shown) is positioned so that when storage vessel 12 is resting against it actuator 21 is positioned just past aperture 30. The user then inserts a finger through aperture 30 in receiver 28 and depresses actuator 21 on storage vessel 12.

Referring to FIG. 7, when actuator 21 is depressed, oxygen is released into the delivery system 14. The user can then inhale oxygen through breathing aperture 38 in second end cap 34 of delivery system 14. Alternatively, user may inhale breathable gas through aperture 30 in delivery system 14. When finished inhaling, the user may return portable oxygen delivery apparatus 10 to its retracted configuration.

Referring to FIGS. 13-15, when using this embodiment of the invention, cap 46 is removed and storage vessel 12 is withdrawn from chamber portion 18 as depicted in FIG. 14.

Mask 48 is then formed by spreading web 50 and connecting members 52 as depicted in FIGS. 14 and 15. Once web 50 and connecting members 52 are spread, chamber portion 18 may be interfaced with the user's facial structure as depicted in FIG. 15.

Referring to FIGS. 16 and 17, in this embodiment of the invention, for transport as depicted in FIG. 16, wings 54 are kept in a closed position. When it is desired to use portable oxygen delivery apparatus 10 in this embodiment, wings 54 are spread as depicted in FIG. 17. Chamber portion 18 may then be brought into close proximity to the user's facial structure to provide for breathing of stored gas.

Referring to FIGS. 18 and 19, in this embodiment of the invention, hinge lid 58 is closed as depicted in FIG. 18 for transport. With hinge lid 58 in this orientation, it is still possible for a user to release stored oxygen or other gas and breathe it from the end of housing 16. When it is desired to cover both the mouth and nose with chamber portion 18, hinge lid 58 may be opened as depicted in FIG. 19. In this orientation, both the mouth and nose of the user may be covered by chamber portion 18 to facilitate breathing the oxygen or other stored gas.

The present invention may be embodied in other specific forms without departing from the spirit of the essential attributes thereof; therefore, the illustrated embodiments should be considered in all respects as illustrative and not restrictive, reference being made to the appended claims rather than to the foregoing description to indicate the scope of the invention.

The invention claimed is:

1. A portable breathable gas delivery apparatus, comprising:
   a pressure vessel for storing the breathable gas under pressure;
   a valve operably coupled to the pressure vessel through which the breathable gas can be selectively released; and
   a housing having a first portion that at least partially encloses the pressure vessel; and
   a second portion that partially encloses a chamber operably coupled to the pressure vessel via the valve into which the breathable gas can be released for breathing by a user, the second portion being structured to cooperate with a user's facial structure to form a substantially closed enclosure, the chamber having an opening adapted to interface with the user's facial structure;
   wherein the second portion extends from the first portion and can be shifted from a folded configuration to an unfolded configuration, wherein the unfolded configuration is adapted for breathing the breathable gas;
   the second portion further comprising a plurality of at least partially rigid panels joined to each other by flexible webs such that the flexible webs are spreadable to separate the at least partially rigid panels by a greater distance at a distal end of the second portion located distal from the first portion of the housing than at a proximal end of the second portion located proximal to the first portion of the housing; and
   wherein the storage vessel is telescopically receivable into the second portion and can be telescopically withdrawn from the second portion.

2. The portable breathable gas delivery apparatus as claimed in claim 1, wherein the opening is formed by a beveled edge of the second portion and is substantially oval in shape.

3. The portable breathable gas delivery apparatus as claimed in claim 1, further comprising a removable end cap joinable to the second portion at least when the second portion is in the folded configuration.

4. The portable breathable gas delivery apparatus as claimed in claim 1, wherein the second portion comprises a storage lid, the storage lid being hingedly attached and shiftable between a first open position and a second closed position.

5. The portable breathable gas delivery apparatus as claimed in claim 1, further comprising a coupling structure whereby the portable breathable gas delivery apparatus can be coupled to another structure for transport.

6. A method of providing breathable gas for delivery to an individual, comprising:
   storing the breathable gas under pressure in a pressure vessel;
   coupling a valve through which the breathable gas can be selectively released to the pressure vessel; and
   at least partially enclosing the pressure vessel in a first portion of a housing having the first portion and a second portion that partially encloses a chamber;
   releasing the breathable gas into the chamber via the valve for breathing; and
   placing an opening of the second portion adapted to interface with the user's facial structure in proximity to the user's facial structure to form a substantially closed enclosure;
   extending the second portion from the first portion;
   shifting the second portion from a folded configuration to an unfolded configuration, wherein the unfolded configuration is adapted for breathing the breathable gas;
   forming the second portion such that it further comprises a plurality of at least partially rigid panels joined to each other by flexible webs, the flexible webs being spreadable such that the at least partially rigid panels are separable at a distal end of the second portion that is distal from the first portion by a greater distance at the distal end than at a proximal end of the second portion that is proximal to the first portion; and
   telescopingly receiving the storage vessel into the second portion or telescopically withdrawing the storage vessel from the second portion.

7. The method as claimed in claim 6, further comprising forming the opening by a beveled edge of the second portion and is substantially oval in shape.

8. The method as claimed in claim 6, further comprising removing a removable end cap from the second portion when the second portion is in the folded configuration.

9. The method as claimed in claim 6, further comprising forming the second portion such that it comprises a storage lid, the storage lid being hingedly attached and shiftable between a first open position and a second closed position.

* * * * *

UNITED STATES PATENT AND TRADEMARK OFFICE
CERTIFICATE OF CORRECTION

| | | |
|---|---|---|
| PATENT NO. | : 7,832,395 B2 | Page 1 of 1 |
| APPLICATION NO. | : 11/715828 | |
| DATED | : November 16, 2010 | |
| INVENTOR(S) | : Bruce Rogers | |

It is certified that error appears in the above-identified patent and that said Letters Patent is hereby corrected as shown below:

Col. 4, line 7, after "is" insert -- a --

Col. 4, line 12, after "is" insert -- a --

Col. 5, line 59, delete "50", insert -- 52 --

Col. 6, line 20, delete "58. Mat", insert -- 58 may --

Signed and Sealed this
Twenty-fourth Day of April, 2012

David J. Kappos
*Director of the United States Patent and Trademark Office*